United States Patent [19]

Laruelle et al.

[11] Patent Number: 5,527,523
[45] Date of Patent: Jun. 18, 1996

[54] HYDROQUINONE AMINO-ACID ESTERS, METHODS OF PREPARATION, AND PHARMACEUTICAL OR COSMETIC COMPOSITIONS CONTAINING THEM

[75] Inventors: Claude Laruelle, Villeneuve-Loubet; Bernard Raynier, Nice; Guy Derrieu, Cagnes-sur-Mer, all of France

[73] Assignee: Virbac S.A., Carros, France

[21] Appl. No.: 917,077

[22] PCT Filed: Feb. 13, 1991

[86] PCT No.: PCT/FR91/00114

§ 371 Date: Oct. 13, 1992

§ 102(e) Date: Oct. 13, 1992

[87] PCT Pub. No.: WO91/11996

PCT Pub. Date: Aug. 22, 1991

[30] Foreign Application Priority Data

Feb. 15, 1990 [FR] France ................. 90 01822

[51] Int. Cl.$^6$ ................ A61K 7/48; A61K 7/00
[52] U.S. Cl. ................ 424/62; 514/166; 514/551
[58] Field of Search ................ 424/62; 514/490, 514/551, 166; 568/663

[56] References Cited

U.S. PATENT DOCUMENTS

| | | | |
|---|---|---|---|
| 4,466,955 | 4/1984 | Calvo | 424/62 |
| 4,518,789 | 5/1985 | Yu | 514/534 |
| 4,526,779 | 7/1985 | Hashimoto | 424/62 |
| 4,764,505 | 8/1988 | Fujinuma | 514/35 |
| 4,876,084 | 10/1989 | Hori | 424/62 |
| 5,001,156 | 3/1991 | Phillipe | 514/534 |
| 5,063,056 | 11/1991 | Yamamoto | 424/401 |

FOREIGN PATENT DOCUMENTS

| | | |
|---|---|---|
| 060092 | 9/1982 | European Pat. Off. . |
| 227531 | 7/1987 | European Pat. Off. . |
| 2192795 | 2/1974 | France . |
| 2577805 | 8/1986 | France . |
| 2456634 | 8/1976 | Germany . |

OTHER PUBLICATIONS

J. S. Bradshaw et al., "Polysiloxanes Containing Thermally Stable Chiral Amide Side–Chains for Capillary Gas ad Supercritical Fluid Chromatography", *Journal of Chromatography*, vol. 405, 18 Sep. 1987, pp. 169–177.

M. S. Matta et al., "Acylation of Subtilisin Carlsberg by Phenyl Esters", *Chemical Abstracts*, vol. 84, No. 17, 26 Apr. 1976, p. 203.

*Primary Examiner*—Thurman K. Page
*Assistant Examiner*—Sally Gardner
*Attorney, Agent, or Firm*—Bell, Seltzer, Park & Gibson

[57] ABSTRACT

Hydroquinone amino-acid esters having formula (I), pharmaceutical or cosmetic compositions containing them, particularly dermatological compositions having pigment-removing activity, and the pharmaceutical, cosmetic or aesthetic uses thereof. The preparation of these novel hydroquinone esters from natural amino-acid derivatives is also described.

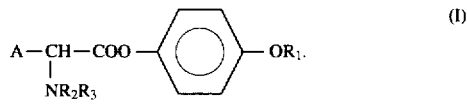

(I)

14 Claims, No Drawings

HYDROQUINONE AMINO-ACID ESTERS, METHODS OF PREPARATION, AND PHARMACEUTICAL OR COSMETIC COMPOSITIONS CONTAINING THEM

The present invention relates to amino acid esters of hydroquinone, to the pharmaceutical or cosmetic compositions in which they are present, in particular the dermatological compositions with depigmenting activity, and to their pharmaceutical, cosmetic or aesthetic applications.

The present invention further relates to the preparation of these novel hydroquinone esters from natural amino acid derivatives.

Hydroquinone and its simple derivatives such as the monomethyl ether and the monobenzyl ether, although currently considered to be among the least irritant of the tyrosinase inhibitors and having an optimal efficacy/tolerance ratio, are nevertheless known to cause irritation and significant sensitization of the skin which is incompatible with prolonged use as a depigmenting agent, either in dermatology or in cosmetology.

In fact, it is imperative for topical depigmenting agents to satisfy three rules: they should have a depigmenting effect only on the lesions to be treated, they should produce neither irritation nor post-inflammatory secondary pigmentation and they should cause neither allergy nor a systemic depigmenting effect.

Some synthetic corticoid or mercury products are active on melanogenesis but have a number of side effects which contraindicate repeated local use.

In order to limit the skin irritation, a number of combinations have been proposed. The combination hydroquinone—vitamin A acid and a corticoid may be mentioned in particular, which has been limited in practice because of the existence of other side effects [J. Invest. Dermatol. 73(5), p. 357, (1979)].

Furthermore, hydroquinone and its simple derivatives have the major disadvantage of being sensitive to oxidation, even in the presence of stabilizers such as ascorbic acid or sodium sulphide [J. Invest. Dermatol. 62, p. 436, (1974)], which results on the one hand in the darkening of the preparations and on the other hand in the generation of entities which are particularly irritant towards the skin, thereby limiting the topical application of hydroquinone and its simple derivatives mentioned above.

To mitigate these different disadvantages, other hydroquinone derivatives have been proposed. French patent no 2 577 805 in the name of SHISEIDO and European patent application no 60092 in the name of SUNSTAR KABUSHIKI KAISHA respectively claim heterosides and $C_1$ to $C_{20}$ carboxylic acid esters of hydroquinone.

However, the products described in both French patent no 2 577 805 and the European patent application have a number of disadvantages; in fact, the products described in French patent no 2 577 805 have an exclusively hydrophilic character which does not allow penetration to the deep layers of the skin where the action of the active principle can be prolonged, and which thus limits the efficacy of these products; as regards the products described in European patent application no 60092, they have an essentially lipophilic character which also limits the efficacy of these products to the extent that their diffusion in contact with the biological fluids is weak.

The object of the present invention was consequently to provide hydroquinone derivatives which meet the practical needs better than the derivatives of the prior art, especially in that they have a remarkable stability to light, heat and water.

The present invention relates to natural amino acid esters of hydroquinone which can have an amphiphilic character, and to the formulations or compositions in which they are present.

These products have the following general formula (I):

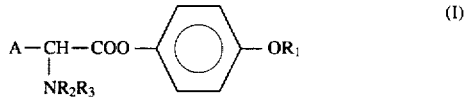

in which:

A is hydrogen, benzyl, an alkyl containing 1 to 4 carbon atoms which is unsubstituted or substituted by one of the following groups: OH, SH, $C_6H_5$—OH, CO—$NH_2$, COOH, $NH_2$, NH—$CNH_2$—$NH_2$, $C_6H_5$, indole, S—$CH_3$, or imidazole, which substituents may themselves be esterified; A corresponds to the radical of a natural alpha-amino acid or a simple derivative thereof, such as a methyl or ethyl ester or a primary amide in the case of dicarboxylic amino acids;

$R_1$ is a hydrogen atom, an alkyl group containing 1 to 6 carbon atoms or a benzyl group;

$R_2$ is a hydrogen atom, an acetyl or benzoyl group or an alkylcarbonyl radical with 2 to 20 hydrocarbon units, or else defines a nitrogen-containing ring with A, with the proviso that $R_2$ is other than a hydrogen atom when A and $R_1$ are methyl groups, that $R_2$ is other than a benzoyl group when A is a hydrogen atom and $R_1$ is a methyl group, and that $R_2$ is other than an acetyl group when A is a benzyl group and $R_1$ is a methyl group; and $R_3$ is a hydrogen atom or, only when A and $R_2$ form a nitrogen-containing ring, an alkylcarbonyl radical with 1 to 20 linear hydrocarbon units or a linear or branched alkyl radical with 1 to 18 hydrocarbon units.

According to an advantageous embodiment of said derivative, A is a hydrogen atom, a nitrogen-containing ring in association with $R_2$, or an alkyl group containing 1 to 4 carbon atoms which is unsubstituted or substituted by one of the following groups: OH, SH, $C_6H_5$—OH, CO—$NH_2$, COOH, $NH_2$, NH—$C(NH_2)$—$NH_2$, $C_6H_5$, indole, S—$CH_3$ or imidazole, which substituents may or may not themselves be esterified.

A thus forms the radical of a natural alpha-amino acid selected especially from alanine, arginine, asparagine, aspartic acid, cysteine, glutamic acid, pyroglutamic acid, glutamine, glycine, histidine, 4-hydroxyproline, isoleucine, leucine, lysine, methionine, ornithine, phenylalanine, proline, serine, threonine, tryptophan, tyrosine and valine.

In terms of the present invention, natural amino acids are understood as meaning the constituent alpha-amino acids of proteins. The chiral site in the alpha-position determines (l) and (d) isomers. General formula (I) includes the (l) isomer and the racemic form of the amino acid. In terms of the present invention, amino acid also covers the simplest derivatives, such as the lower alkyl monoesters in the case of dicarboxylic amino acids.

In terms of the present invention, alkyl includes especially methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

The Applicant has found that, surprisingly, the products of general formula (I) have a depigmenting activity at least comparable to and in most cases greater than that of hydroquinone and its simple derivatives, without having the disadvantages of the products of the prior art; in fact, the products of the present invention unexpectedly have a remarkable stability to light, heat and water and can be appropriately mixed with all kinds of hydrophilic and lipophilic pharmaceutical and cosmetic base materials.

According to an advantageous provision of this embodiment, A forms, with $R_2$, products containing a pyrrolidin-2-one ring which have the following formula (II):

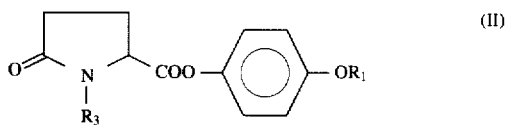

in which $R_1$ and $R_3$ are as defined above.

In the products of formula (II) according to the invention, A thus defines a pyroglutamic acid radical with $R_2$.

A number of documents describe the value of the pyroglutamic acid radical in the field of dermatology and cosmetics, and especially the fact that the sodium salt of (l)-pyroglutamic acid prevents dehydration of the skin and makes it soft, supple and elastic (J. Soc. Cosmet. Chem. (1984) 35(3) 171); French patent no 2 122 495 in the name of the company KARL THOMAE claims the use of aliphatic pyroglutamates in skin treatment and hygiene; in its European patent application no 176 217, UNILEVER proposes the use of (l)-pyroglutamic acid esters in preparations for topical use, in particular for the treatment of sunburn, acne and hyperkeratosis; in its European patent no 227 531, MERCK claims the use of pyroglutamates as vehicles which greatly increase the penetration of drugs through the skin, and in its European patent application no 123 943, the Japanese company TEIJIN describes glycerol pyroglutamates.

However, in the esters of formula (II) according to the invention, the unexpected property of high stability is coupled with a prolonged action on the skin's moisture.

The Applicant is of the opinion that this unexpected action is due to the fact that the products of formula (II) are analogous to the natural peptides containing a pyroglutamic acid radical, and that they are therefore preferred substrates for the enzyme which effects one step of the synthesis of the pyroglutamic acid present in the stratum corneum. The esters of formula (II) according to the invention easily penetrate this zone and help to ensure that it contains a consequent level of pyroglutamic acid. The latter, which is produced inside the cells of the stratum corneum, is very insensitive to removal by washing, as is the active entity released by hydrolysis. Said active entity is therefore capable of having a prolonged depigmenting action.

The products according to the invention are capable of being used as depigmenting agents.

The present invention further relates to a depigmenting agent, characterized in that it consists of a natural amino acid ester of hydroquinone of the following formula (I):

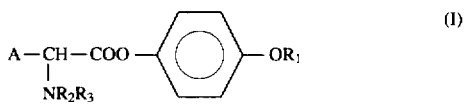

in which:

A corresponds to the radical of a natural alpha-amino acid or a simple derivative thereof, such as a methyl or ethyl ester or a primary amide in the case of dicarboxylic amino acids;

$R_1$ is a hydrogen atom, an alkyl group containing 1 to 6 carbon atoms or a benzyl group;

$R_2$ is a hydrogen atom, an acetyl or benzoyl group or an alkylcarbonyl radical with 2 to 20 hydrocarbon units, or else defines a nitrogen-containing ring with A, including the case where $R_2$ is a hydrogen atom and A and $R_1$ are methyl groups, the case where $R_2$ is a benzoyl group, A is a hydrogen atom and $R_1$ is a methyl group, and the case where $R_2$ is an acetyl group, A is a benzyl group and $R_1$ is a methyl group; and $R_3$ is a hydrogen atom or, only when A and $R_2$ form a nitrogen-containing ring, an alkylcarbonyl radical with 1 to 20 linear hydrocarbon units or a linear or branched alkyl radical with 1 to 18 hydrocarbon units.

The products according to the invention are capable of being associated with vehicles appropriate for the preparation of pharmaceutical and/or cosmetic compositions which are particularly effective in the treatment of undesirable hyperpigmentations due to melanin, and especially freckles (ephelides), the mask of pregnancy (chloasma), liver spots or senile lentigo, post-traumatic or post-lesional hyperpigmentations, and phototoxicity reactions due in particular to perfumes.

The same compositions are also particularly useful for subjects who consider their complexion to be too dark and wish to lighten it.

The present invention further relates to a method of aesthetic treatment for humans to modify the skin's pigmentation, comprising the topical administration of an appropriate amount of depigmenting agent according to the invention.

The pharmaceutical and/or cosmetic compositions according to the present invention do not cause appreciable skin irritation and do not sensitize the skin, so they can be applied continuously over a long period of time.

The compounds of general formula (I) can be used indiscriminately in the appropriate preparations for application to the skin, such as ointments, creams, aerosols, powders, tinctures, gels, pastes or lotions. As active ingredient, the corresponding preparations have one or more of the compounds of general formula (I), either as such or in the form of pharmaceutically acceptable salts. These active ingredients are normally present in proportions of 0.01 to 20% by weight, preferably of 0.1 to 10% by weight. In fact, it should be noted that if the proportion of active ingredient exceeds 20%, this does not result in a corresponding improvement, and that if the proportion is below 0.01%, the envisaged effects are no longer guaranteed.

The compositions according to the present invention can contain any of the conventional ingredients commonly used in cosmetic or pharmaceutical compositions for treating the skin. Examples of these ingredients are:

natural or synthetic oils such as liquid paraffin, castor oil, squalane and coconut oil;

antioxidants such as butylhydroxyanisole, butylhydroxytoluene, ethyl gallate and tocopherol;

surfactants such as sodium laurate, laurylpyridinium chloride, polyoxyethylene sorbitan monooleate, sodium N-stearyl-N,N-dimethylglycine and polyoxypropylene glyceryl ether phosphate;

humectants such as glycerol, sodium pyroglutamate and sodium lactate;

thickeners such as gum tragacanth, quince seed gum, xanthane gum, carboxyvinyl polymer and bentonite;

preservatives such as benzoic acid, alkyl p-hydroxybenzoates, dehydroacetic acid and trichlorocarbanilide;

colourants and pigments such as acid red, rhodamine B, violamine R, orange SS, naphthol, yellow S, tartrazine, alizarin, cyanine green F, acid violet, carthamine, blue and yellow iron oxide, titanium dioxide, cobalt blue, pink blue and ultramarine violet, and carbon black;

waxes such as beeswax, Japan wax, carnauba wax, candelilla wax and lanolin;

film-forming agents such as nitrocellulose and polyvinyl alcohol;

solvents such as water and alcohols, for example ethanol;

powders such as aluminium powder, talc, kaolin, zinc oxide, titanium dioxide, mica and calcium carbonate;

plasticizers such as acetyltributyl citrate and dibutyl phthalate;

substances which filter out UV radiation, such as those of the following types: p-aminobenzoic acid and corresponding esters, salicylate, cinnamate and benzophenone derivatives; and fragrances such as musk, civet, amber, jasmin and rose oil.

The compounds of general formula (I):

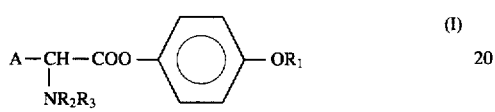

can be prepared according to the known techniques, among which there may be mentioned:

a) Activation of the carboxylic acid group of an amino acid protected on the nitrogen by a benzyloxycarbonyl radical, and reaction with a derivative p—OH—$C_6H_4$—$OR_1$, where $R_1$, here and in the following text, is as defined above. The reagents for activating the carboxylic acid group are selected from 1,1-carbonyldiimidazole, 1,1-carbonyldi(1,2,4-triazole), N-hydroxyphthalimide and N-hydroxysuccinimide, preferably 1,1-carbonyldiimidazole. The protecting group is removed under mild conditions by catalytic hydrogenolysis carried out in an inert solvent—a secondary alcohol or acetic acid—to give the compounds of general formula (III):

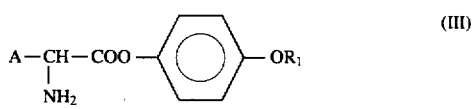

b) Acylation of an amino acid in a two-phase water/organic solvent medium with a reactive derivative of the acid $R_2OH$ ($R_2$ being an alkylcarbonyl radical as defined above), preferably the corresponding chloride. The resulting product can also be prepared by acylation of the benzyl ester of the corresponding amino acid with the same reactive derivative, in an organic medium, in the presence of an acid acceptor, followed by hydrogenolysis. The resulting product is activated before reaction with a derivative p—OH—$C_6H_4$—$OR_1$, as explained in section a), to give the compounds of formula (IV):

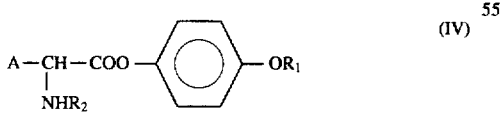

c) Acylation of the corresponding amino acid—when A and $R_2$ form a nitrogen-containing ring—with a reactive derivative of the acid $R_3OH$ ($R_3$ being an alkylcarbonyl radical as defined above) according to the modalities mentioned in section b).

Alkylation of the sodium salt of the benzyl ester of the corresponding amino acid—when $R_3$ is an alkyl radical as defined above and A and $R_2$ form a nitrogen-containing ring—is carried out with a reactive derivative $R_3X$, X being a halogen, preferably bromine. This alkylation is followed by hydrogenolysis. The sodium salt is generally prepared in situ via sodium hydride or methylate.

The products obtained, which are characterized by formula (V) below:

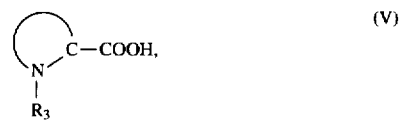

are activated before reaction with a derivative p—OH—$C_6H_4$—$OR_1$, as explained in section a), to give the compounds of formula (II).

d) Finally, to obtain the compounds of formula (II) in which $R_3$ is hydrogen, a simple and efficient technique is used which consists in carrying out a direct fusion of the corresponding amino acid with the derivative p—OH—$C_6H_4$—$OR_1$, without a solvent and under an inert atmosphere.

In general, the reactants are employed in stoichiometric ratios; the reactions are carried out in solvents which are inert towards the reactants, such as chloroform, methylene chloride, dioxane or dimethylformamide. The acid acceptors are generally tertiary nitrogen bases, preferably pyridine or triethylamine.

In addition to the foregoing provisions, the invention also includes other provisions which will become apparent from the following description.

The Examples which follow are illustrations of the compounds of formula (I), the various preparative methods detailed above, the dermatological or cosmetic compositions in which they are present and the tests for evaluation of these compositions.

It must be clearly understood, however, that these Examples of execution and of experimental reports are given solely in order to illustrate the subject of the invention, without in any way implying a limitation.

All the products obtained were subjected to analysis by thin layer chromatography (TLC) and only show a single spot. The TLCs were run on F 254 silica gel plates and developed in the following systems:

(i): toluene 10; ethyl formate 10; formic acid 1.

(ii): benzene 30; methanol 1.

(iii): n-butanol 8; acetic acid 1; water 1.

The results of the percentage analyses performed on all the products are consistent with the theoretical formulae.

EXAMPLE I

4-HYDROXYPHENOL (L)-PYROGLUTAMATE 129 g (1 mol) of (l)-pyroglutamic acid and 110 g (1 mol) of hydroquinone are intimately mixed, the mixture is stirred at 175° under a stream of nitrogen for 18 hours, the temperature is lowered to 50° and the mixture is diluted with water (300 ml) and extracted with ethyl acetate (3×400 ml). A crude product is thus prepared which is purified by being made into a paste twice with ethyl acetate (250 ml) to give the title derivative in the form of crystals melting at 179°/82°. In TLC, the product shows a single spot of Rf(i)=0.33.

EXAMPLE II

4-HYDROXYPHENOL N-HEXADECANOYL-(L)-ALANINATE a): N-Hexadecanoyl-(l)-alanine:

The title derivative is obtained by the acylation of (l)-alanine with a stoichiometric amount of hexadecanoyl chloride in a two-phase water/ethyl ether medium, in the presence of sodium carbonate and 10% sodium hydroxide solution. It takes the form of crystals melting at 94°/7° and shows a single spot of Rf(i)=0.60 in TLC.

b): 4-Benzyloxyphenol N-hexadecanoyl-(l)-alaninate:

16.4 g (0.05 mol) of N-hexadecanoyl-(l)-alanine and 8.1 g (0.05 mol) of 1,1-carbonyldiimidazole are dissolved in 100 ml of dimethylformamide, the solution is stirred at 5° for 1 hour, 10 g (0.05 mol) of 4-benzyloxyphenol in 50 ml of dimethylformamide are run in, the mixture is stirred for 18 hours and evaporated and the residue is then taken up with chloroform. After washes with water and dilute sodium hydroxide solution and drying, the title derivative is obtained in the pure state, m.p.=77°/9°, and only shows a single spot of Rf(i)=0.76 in TLC.

c): 4-Hydroxyphenol N-hexadecanoyl-(l)-alaninate:

The product obtained is subjected to hydrogenolysis in acetic acid in the presence of palladium-on-charcoal. When the reaction is complete, the mixture is filtered, the filtrate is evaporated and the residue is recovered in ethyl ether to give the title derivative in the form of crystals melting at 66°/7°; it only shows a single spot of Rf(i)=0.49 in TLC.

EXAMPLES III TO XV

The following products are prepared under the conditions described above:

III: 4-benzyloxyphenol N-benzoylglycinate: m.p.=138°/40°

IV: 4-hydroxyphenol N-benzoylglycinate: m.p.=149°/51°

V: 4-methoxyphenol N-hexadecanoyl-(l)-alaninate: m.p.=70°/1°

VI: 4-methoxyphenol N-octyl-(l)-pyroglutamate: m.p.=95°/7°

VII: 4-methoxyphenol N-hexanoyl-(l)-pyroglutamate: m.p.=103°/5°

VIII: 4-hydroxyphenol (l)-alaninate: m.p.= 154°/8°

IX: 4-benzyloxyphenol N-decanoyl-(l)-valinate: m.p.=88°/9°

X: 4-hydroxyphenol N-decanoyl-(l)-valinate: m.p.=64°/6°

XI: 4-methoxyphenol N-decanoyl-(l)-valinate: m.p.=81°/3°

XII: 4-benzyloxyphenol N-dodecanoyl-(l)-leucinate: m.p.=80°/2°

XIII: 4-hydroxyphenol N-dodecanoyl-(l)-leucinate: m.p.=61°/3°

XIV: 4-methoxyphenol N-octadecanoyl-(l)-valinate: m.p.=66°/8°

XV: 4-hydroxyphenol N-hexanoyl-γ-methyl-(l)-glutamate: m.p.=102°/5°

EXAMPLE XVI

DEPIGMENTING COMPOSITION NO 1:

| Ingredients | % |
| --- | --- |
| Stearic acid | 6 |
| Stearyl alcohol | 5 |
| Butyl stearate | 8 |
| Glycerol monostearate | 2 |
| Octyl cinnamate | 2 |
| Propylene glycol | 10 |
| Product according to Example X | 6.5 |
| Potassium hydroxide | 0.2 |
| Methyl p-hydroxybenzoate | 0.09 |
| Propyl p-hydroxybenzoate | 0.01 |
| Butylhydroxytoluene | 0.02 |
| Demineralized water | qs 100 |

The propylene glycol and the potassium hydroxide are dissolved in the water and the aqueous phase is heated to a temperature of 70°. The other ingredients are mixed together, melted by heating and kept at a temperature of about 70°. The oily phase is added to the aqueous phase and the mixture is emulsified with a homogenizer. The product is cooled to room temperature, with stirring.

EXAMPLE XVII

DEPIGMENTING COMPOSITION NO 2:

| Ingredients | % |
| --- | --- |
| Beeswax | 10 |
| Ceresin | 7 |
| White petrolatum | 3 |
| Hydrated lanolin | 2 |
| Isopropyl myristate | 2 |
| Squalane | 2 |
| Liquid paraffin | 40 |
| Polyoxyethylene cetyl ether | 2 |
| Product according to Example I | 4 |
| Glycerol monostearate | 2 |
| Propylene glycol | 2 |
| Butylhydroxytoluene | 0.02 |
| Demineralized water | qs 100 |

The preparation is carried out according to Example XVI.

EXAMPLE XVIII

DEPIGMENTING COMPOSITION NO 3:

| Ingredients | % |
| --- | --- |
| Ethyl alcohol (95%) | 30 |
| Dipropylene glycol | 18 |
| Polyoxyethylene oleyl ether | 2.5 |
| Carboxyvinyl polymer | 1.5 |
| Potassium hydroxide | 0.2 |
| (1)-Arginine | 0.15 |
| Product according to Example XIII | 7.5 |
| Methyl p-hydroxybenzoate | 0.09 |
| Propyl p-hydroxybenzoate | 0.01 |
| Demineralized water | qs 100 |

The carboxyvinyl polymer is dissolved in the water, and the dipropylene glycol, the oleyl ether, the product according to Example XIII and the preservatives are dissolved in the ethanol. The alcoholic solution is added to the aqueous solution and the resulting solution is neutralized and thickened with the potassium hydroxide and the (l)-arginine.

EXAMPLE XIX

RESULTS OF THE TESTS FOR EVALUATION OF THE COMPOSITIONS ACCORDING TO EXAMPLES XVI to XVIII

The corresponding compositions have a potential hydroquinone content of 2%. They are compared with a composition no 4 prepared according to Example XVI but containing 2% of hydroquinone in place of the product according to Example X.

a) Depigmenting activity:

This is evaluated by application of the samples to 20 subjects suffering from chloasma. Each of the subjects applies the 4 compositions to 4 different zones, morning and evening, at a rate of 0.2 g each time, each zone receiving the same product throughout the treatment period of 8 weeks.

The improvements are observed visually each week, the experimenter also assessing the tolerance to the treatment by noting any manifestations on the skin or elsewhere which may originate from the treatment being applied. It was thus possible to note the particular value of the compositions according to the invention, which are perfectly tolerated and have a very significant depigmenting activity.

Table I below shows the results obtained at the end of the treatment.

TABLE I

| Notation (*) | Composition no 1 | Composition no 2 | Composition no 3 | Composition no 4 |
|---|---|---|---|---|
| XXX | 4 | 4 | 3 | 2 |
| XX | 11 | 9 | 10 | 8 |
| X | 5 | 8 | 6 | 8 |
| 0 | 0 | 1 | 1 | 2 |

(*)XXX: remarkable improvement
XX: substantial improvement
X: slight improvement
o: no improvement b) Stability:

The change in colouration of compositions 1 and 4 is observed by storing the samples at 37° for 12 weeks. The modifications are evaluated visually and are shown in Table II below, which confirms the remarkable stability of the composition containing a compound according to the invention.

TABLE II

| | Storage time (weeks) | | | | |
|---|---|---|---|---|---|
| Composition | 1 | 3 | 6 | 9 | 12 |
| 1 | 0 | 0 | 0 | 0 | 0 |
| 4 | X | XX | XXX | XXX | XXX |

(*)0: no change
X: slight darkening
XX: substantial darkening
XXX: considerable darkening

EXAMPLE XX

ASSESSMENT OF THE SUPERFICIAL AND PERCUTANEOUS TOLERANCE BY ITERATIVE APPLICATIONS

Compositions no 2 and no 4, composition no 5 prepared according to Example XVII with 4% of hydroquinone monohexanoate in place of the product according to Example I, and composition no 6 prepared according to Example XVIII with 5% of arbutin in place of the product according to Example XIII, were compared.

2 g of product is applied daily, for 42 consecutive days, to the skin in the postscapular dorsal region of 24 rabbits shaved regularly every 7 days, using 6 rabbits per composition, said product being caused to penetrate by gentle massage.

The erythema and the formation of oedema are preferentially assessed according to the following numerical scale:
no erythema (or no oedema): 0
scarcely visible, slight erythema (or very slight oedema): 1
clearly visible erythema (or slight oedema): 2
substantial erythema (or substantial oedema): 3

The results are collated in Table III, which shows the number of rabbits corresponding to each evaluation.

TABLE III

| COMPOSITION No | DURATION (weeks) | ERYTHEMA | | | | OEDEMA | | | |
|---|---|---|---|---|---|---|---|---|---|
| | | 0 | 1 | 2 | 3 | 0 | 1 | 2 | 3 |
| 2 | 2 | 6 | | | | 6 | | | |
| | 6 | 5 | 1 | | | 6 | | | |
| 4 | 2 | | 1 | 3 | 2 | | 2 | 3 | 1 |
| | 6 | | | 2 | 4 | | | 2 | 4 |
| 5 | 2 | 1 | 2 | 3 | | 2 | 4 | | |
| | 6 | | 2 | 3 | 1 | 1 | 3 | 2 | |
| 6 | 2 | 6 | | | | 5 | 1 | | |
| | 6 | 4 | 2 | | | 4 | 2 | | |

During this study, the appearance and suppleness of the skin, the rate and appearance of hair growth and the thickness of the skin cover were also assessed once a week.

All these observations, together with the results shown in Table III, clearly indicate the particular value of the products according to the invention compared with the other depigmenting agents.

EXAMPLE XXI

ASSESSMENT OF RETENTION IN THE SUBCUTANEOUS TISSUES

Compositions no 3 and no 6 are compared on six rats, using three rats per composition, in a single administration of 1 g/rat, on a previously shaved and perfectly delimited dorsal zone. After 8 hours, the exposed zone is washed with a piece of cotton-wool soaked in alcohol, the animals are sacrificed and the tissues corresponding to the dermis, epidermis and stratum corneum are excised, homogenized, treated and extracted for HPLC assay in equivalents of the active principle (AP) used. The results are reported in Table IV.

TABLE IV

| COMPOSITION No | DOSE g/rat | DOSE OF AP mg | Equivalent amount of AP (a) accumulated |
|---|---|---|---|
| 3 | 1 | 40 | 2.5 (±0.85) |
| 6 | 1 | 50 | 0.45 (±0.12) |

(a): expression in mg/g of tissue

These results, combined with the data collated in Examples XIX and XX, confirm the particular value of the products according to the invention compared with hydroquinone glucosides.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. A hydroquinone derivative compound, characterized in that it is constituted by an amino acid ester of hydroquinone and in that it has the following formula (I):

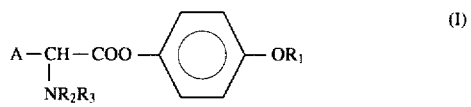

A is a hydrogen atom, or A in association with N and $R_2$ form a nitrogen-containing ring, or an alkyl group containing 1 to 4 carbon atoms which is unsubstituted or substituted by one of the following substituents: OH, SH, $C_6H_4$—OH, CO—$NH_2$, COOH, $NH_2$, NH—C(NH)—$NH_2$, $C_6H_5$, indole, S—$CH_3$ or imidazole, which substituents may or may not themselves be esterified; A forming a radical of an alpha-amino acid or a derivative of an alpha-amino acid chosen from the group consisting of a methyl or an ethyl ester of a dicarboxylic alpha-amino acid and a primary amide of a dicarboxylic alpha-amino acid;

$R_1$ is a hydrogen atom, an alkyl group containing 1 to 6 carbon atoms or a benzyl group;

$R_2$ is a hydrogen atom, an acetyl or benzoyl group or an alkylcarbonyl radical with 2 to 20 hydrocarbon units, or else defines a nitrogen-containing ring with A, with the proviso that $R_2$ is other than a hydrogen atom when A and $R_1$ are methyl groups, that $R_2$ is other than a benzoyl group when A is a hydrogen atom and $R_1$ is a methyl group, and that $R_2$ is other than an acetyl group when A is a benzyl group and $R_1$ is a methyl group; and $R_3$ is a hydrogen atom or, only when A and $R_2$ form a nitrogen-containing ring, an alkylcarbonyl radical, branched alkyl radical with 1 to 20 linear hydrocarbon units or a linear or branched alkyl radical with 1 to 18 hydrocarbon units, said hydroquinone derivative having an amphophilic character.

2. A derivative according to claim 1, characterized in that A forms, with $R_2$, compounds containing a pyrrolidin-2-one ring, A thus defining a pyroglutamic acid radical with $R_2$, which compounds have the following formula (II):

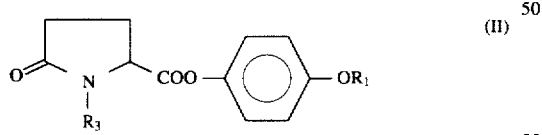

in which $R_1$ and $R_3$ are as defined above.

3. A derivative according to claim 1, characterized in that the radical $R_2$ is an alkylcarbonyl radical.

4. A derivative according to claim 1, characterized in that the radical $R_3$ is an alkyl group.

5. A derivative according to claim 1, characterized in that the radical $R_3$ is an alkylcarbonyl radical.

6. A pharmaceutical composition, characterized in that it comprises a hydroquinone derivative according to claim 1, in proportion of 0.01 to 20% by weight, in association with a pharmaceutically acceptable vehicle.

7. A pharmaceutical composition, useful as a depigmenting agent, characterized in that it comprises a hydroquinone derivative according to claim 1, proportion of 0.01 to 20% by weight.

8. A method of preparing a pharmaceutical or cosmetic composition having depigmenting action, said method comprising combining a hydroquinone derivative of formula (I) according to claim 1, which has the following formula (I'):

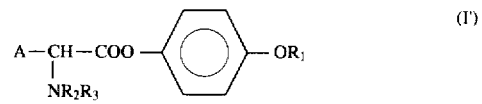

in which A, $R_1$ and $R_3$ have the same meaning as above and in which:

if $R_2$ is a hydrogen atom, A and $R_1$ are methyl groups or if $R_2$ is a benzoyl group, A is a hydrogen atom and $R_1$ is a methyl group or if $R_2$ is an acetyl group, A is a benzyl group and $R_1$ is a methyl group, with a pharmaceutically acceptable vehicle.

9. A composition according to claim 6, characterized in that it contains from 0.1 to 10% by weight of a compound of formula (I).

10. A method for treating humans to modify the skin's pigmentation to lighten the skin, comprising topically applying a pharmaceutically effective amount of a compound selected from the group consisting of compounds of formula (I) and the compounds of formula (I'):

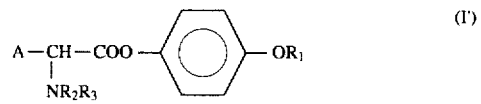

in which A, $R_1$ and $R_3$ have the same meaning as above and in which:

if $R_2$ is a hydrogen atom, A and $R_1$ are methyl groups or if $R_2$ is a benzoyl group, A is a hydrogen atom and $R_1$ is a methyl group or if $R_2$ is an acetyl group, A is a benzyl group and $R_1$ is a methyl group, in association with a pharmaceutically acceptable vehicle.

11. The method according to claim 10, characterized in that the compound of formula (I) or the compound of formula (I') is in the form of a composition comprising 0.01 to 20% by weight of said compound.

12. The method according to claim 11, characterized in that said compounds are in the form of a composition comprising 0.1 to 10% by weight of said compounds.

13. A method of using the hydroquinone derivative according to claim 1 wherein the compound of formula (I) has the formula (I'):

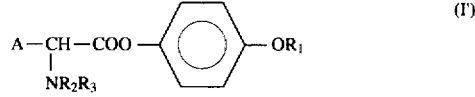

wherein when $R_2$ is a hydrogen atom, A and $R_1$ are methyl groups;

when $R_2$ is a benzoyl group, A is a hydrogen atom and $R_1$ is a methyl group;

and when $R_2$ is an acetyl group, A is a benzyl group and $R_1$ is a methyl group as a cosmetic product, said method comprising topically applying said compound of formula (I') to skin.

14. A cosmetic composition comprising the hydroquinone derivative according to claim 1 in proportion of 0.01 to 20% by weight of said hydroquinone derivative and a pharmaceutically acceptable vehicle.

* * * * *

UNITED STATES PATENT AND TRADEMARK OFFICE
CERTIFICATE OF CORRECTION

PATENT NO. : 5,527,523
DATED : June 18, 1996
INVENTOR(S) : Claude Laruelle et al It is certified that error appears in the above-indentified patent and that said Letters Patent is hereby corrected as shown below:

On the cover page, Section [56] References Cited:

Under U.S. Patent Documents:

"Calvo" should be -- Calvo et al. --
"Fujinuma" should be -- Fujinuma et al. --
"Hori" should be -- Hori et al. --
"Phillipe" should be -- Philippe et al. --

Under "Other Publications":

"Polysiloxanes Containing Thermally Stable Chiral Amide Side-Chains for Capillary Gas ad Supercritical Fluid Chromatography" should be -- "Polysiloxanes Containing Thermally Stable Chiral Amide Side-Chains for Capillary Gas and Supercritical Fluid Chromatography" --

Column 12, line 1, --in -- should be inserted after "claim 1, ".

Signed and Sealed this

Tenth Day of December, 1996

Attest:

BRUCE LEHMAN

Attesting Officer

Commissioner of Patents and Trademarks